US010053768B2

United States Patent
Senowitz (10) Patent No.: US 10,053,768 B2
(45) Date of Patent: Aug. 21, 2018

(54) DETACHING PROBE FROM TEM SAMPLE DURING SAMPLE PREPARATION

(71) Applicant: FEI Company, Hillsboro, OR (US)

(72) Inventor: Corey Senowitz, San Diego, CA (US)

(73) Assignee: FEI Company, Hillsboro, OR (US)

( * ) Notice: Subject to any disclaimer, the term of this patent is extended or adjusted under 35 U.S.C. 154(b) by 821 days.

(21) Appl. No.: 14/456,946

(22) Filed: Aug. 11, 2014

(65) Prior Publication Data
US 2015/0075972 A1    Mar. 19, 2015

Related U.S. Application Data (60) Provisional application No. 61/865,929, filed on Aug. 14, 2013.

(51) Int. Cl.
| | |
|---|---|
| C23C 14/00 | (2006.01) |
| C23C 14/30 | (2006.01) |
| G01N 1/32 | (2006.01) |
| H01J 37/305 | (2006.01) |

(52) U.S. Cl.
CPC ............. *C23C 14/30* (2013.01); *G01N 1/32* (2013.01); *H01J 37/3056* (2013.01); *H01J 2237/208* (2013.01); *H01J 2237/304* (2013.01); *H01J 2237/31745* (2013.01)

(58) Field of Classification Search
CPC ............................ C23C 14/30; H01J 37/3056
USPC ................... 250/307, 310, 311, 492.1–492.3
See application file for complete search history.

(56) References Cited

U.S. PATENT DOCUMENTS

| | | | | |
|---|---|---|---|---|
| 6,538,254 B1 * | 3/2003 | Tomimatsu | ......... | H01J 37/3056 250/442.11 |
| 6,870,161 B2 * | 3/2005 | Adachi | ................. | G01N 1/286 250/310 |
| 7,511,282 B2 * | 3/2009 | Agorio | ................... | G01N 1/286 216/2 |
| 8,134,124 B2 | 3/2012 | Blackwood et al. | | |
| 8,357,913 B2 | 1/2013 | Agorio et al. | | |
| 8,525,137 B2 | 9/2013 | Blackwood et al. | | |
| 8,536,525 B2 | 9/2013 | Blackwood et al. | | |
| 8,835,845 B2 * | 9/2014 | Hong | .................. | H01J 37/3056 250/307 |

(Continued)

FOREIGN PATENT DOCUMENTS

| | | |
|---|---|---|
| CN | 102809496 A | 12/2012 |
| EP | 927880 A1 | 7/1999 |

(Continued)

OTHER PUBLICATIONS

Herlinger, L.R., et al, "TEM Sample Preparation Using a Focused Ion Beam and a Probe Manipulator," Symposium for Testing and Failure Analysis, 1996, pp. 199-205.

(Continued)

*Primary Examiner* — John J Brayton
(74) *Attorney, Agent, or Firm* — Scheinberg & Associates, PC; Michael O. Scheinberg (57) ABSTRACT

An improved method of preparing a TEM sample. A sample is extracted from a work piece and attached to a probe for transport to a sample holder. The sample is attached to the sample holder using charged particle beam deposition, and mechanically separated from probe by moving the probe and the sample holder relative to each other, without severing the connection using a charged particle beam.

14 Claims, 5 Drawing Sheets

(56) References Cited

U.S. PATENT DOCUMENTS

| | | | |
|---|---|---|---|
| 8,859,998 B2* | 10/2014 | Blackwood | G01N 1/286 250/492.1 |
| 2004/0129897 A1 | 7/2004 | Adachi et al. | |
| 2007/0278421 A1* | 12/2007 | Gleason | G01N 1/286 250/442.11 |
| 2012/0119084 A1 | 5/2012 | Shaapur et al. | |
| 2013/0153785 A1 | 6/2013 | Agorio et al. | |

FOREIGN PATENT DOCUMENTS

| | | |
|---|---|---|
| EP | 2151847 A1 | 2/2010 |
| JP | 3547143 B2 | 7/2004 |
| JP | 2007316073 A | 12/2007 |
| JP | 2009014709 A | 1/2009 |
| JP | 2010507882 A | 3/2010 |
| JP | 2012252004 A | 12/2012 |
| JP | 2013057533 A | 3/2013 |
| WO | WO2008049134 A2 | 4/2008 |
| WO | 2012103534 A1 | 8/2012 |

OTHER PUBLICATIONS

Ebel, J., et al, "Cross-sectional Atomic Force Microscopy of Focused Ion Beam Milled Devices," IEEE, Reliability Physics Symposium Proceedings, 1998, pp. 157-162.

\* cited by examiner

DETACHING PROBE FROM TEM SAMPLE DURING SAMPLE PREPARATION

CROSS-REFERENCE TO RELATED APPLICATIONS

This Application claims priority from U.S. Provisional Application 61/865,929, filed Aug. 14, 2013, which is hereby incorporated by reference.

TECHNICAL FIELD OF THE INVENTION

The present invention relates to preparation of samples for transmission electron microscopes and, in particular, to preparation of samples in a vacuum chamber using a focused ion beam.

BACKGROUND OF THE INVENTION

As semiconductor geometries continue to shrink, manufactures increasingly rely on Transmission electron microscopes (TEMs) for monitoring the process, analyzing defects, and investigating interface layer morphology. Transmission electron microscopes (TEMs) allow observers to see features having sizes on the order of nanometers. In contrast to SEMs, which only image the surface of a material, TEM also allows analysis of the internal structure of a sample. In a TEM, a broad beam impacts the sample and electrons that are transmitted through the sample are focused to form an image of the sample. The sample must be sufficiently thin to allow many of the electrons in the primary beam to travel though the sample and exit on the opposite site.

Because a sample must be very thin for viewing with transmission electron microscopy (whether TEM or STEM), preparation of the sample can be delicate, time-consuming work. The term "TEM" as used herein refers to a TEM or a STEM and references to preparing a sample for a TEM are to be understood to also include preparing a sample for viewing on an STEM. The term "STEM" as used herein also refers to both TEM and STEM.

The viewing area of TEM samples are typically less than 100 nm thick, but for some applications samples must be considerably thinner. With advanced processes at 30 nm and below, the sample needs to be less than 20 nm in thickness in order to avoid overlap among small scale structures.

Even though the information that can be discovered by TEM analysis can be very valuable, the entire process of creating and measuring TEM samples has historically been so labor intensive and time consuming that it has not been practical to use this type of analysis for manufacturing process control. While the use of FIB methods in sample preparation has reduced the time required to prepare samples for TEM analysis down to only a few hours, it is not unusual to analyze 15 to 50 TEM samples from a given wafer. As a result, speed of sample preparation is a very important factor in the use of TEM analysis, especially for semiconductor process control.

A conventional method of preparing TEM samples using a focused ion beam is described in U.S. Pat. No. 6,538,254 to Tomimatsu et al. for "Method and Apparatus for Specimen Fabrication." A sample is separated from a work piece using charged particle beam milling. A probe is attached to the sample prior to separation using charged particle beam deposition or sputter deposition. The sample is then freed from the work piece and transported on the probe to a sample holder. The sample is attached to the sample holder by ion beam deposition, and then the sample is transported to a sample holder. The sample is attached to the sample holder using ion beam deposition, and then the probe is freed from the sample by ion beam milling. Each step of ion beam deposition and ion beam milling is time consuming.

Thus, there is still a need for an improved, more efficient method to prepare samples for viewing on a TEM.

SUMMARY OF THE INVENTION

It is an object of the invention, therefore, to provide an improved method of preparing TEM samples.

In a preferred embodiment, a sample is freed from a work piece using ion beam etching. The sample is attached to a probe using charged particle beam deposition. The sample is moved to a sample holder, and the sample is attached to the sample holder. The probe is then detached from the sample by moving the probe relative to the sample holder, breaking the connection without using an ion beam to sever the connection.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION OF PREFERRED EMBODIMENTS

Figure 1:
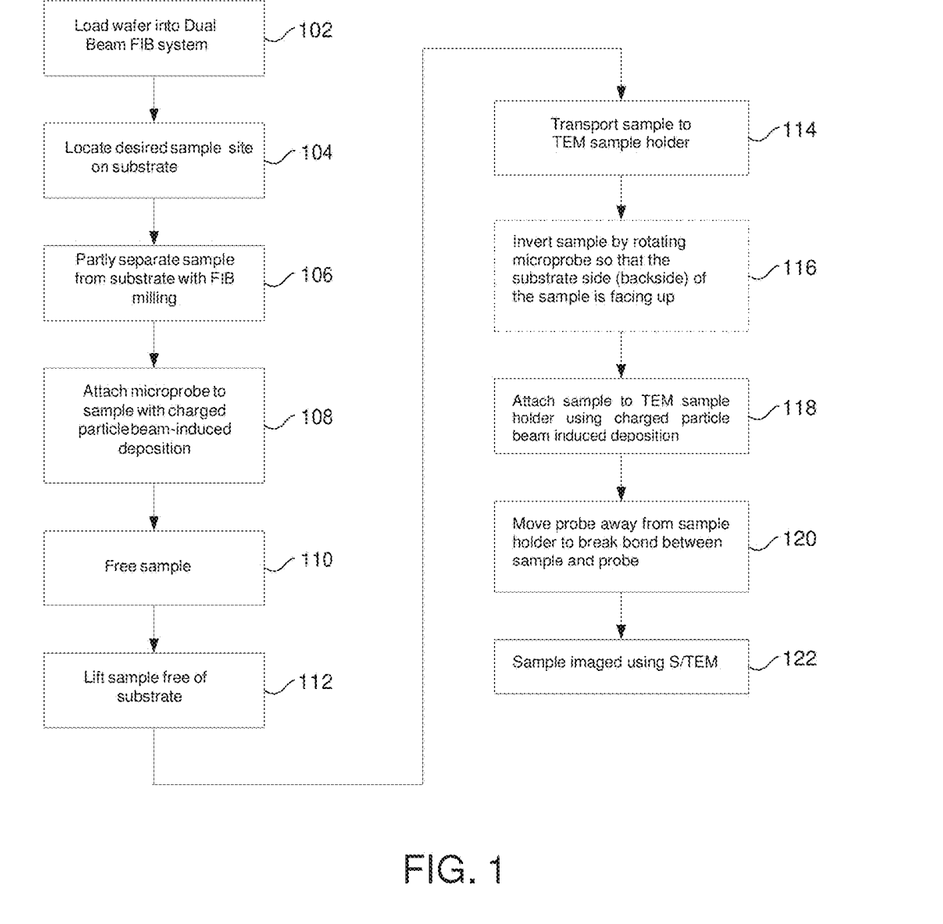
FIG. 1 is a flow chart of the steps of an embodiment of the invention.

Embodiments of the present invention are directed at a novel method of preparing TEM samples. FIG. 1 is a flowchart showing the steps of creating a TEM sample according to a one embodiment of the present invention. Various steps in the process are shown in FIGS. 2 through 5D. The invention is applicable to the preparation of any type of sample that is attached to a probe for transporting to a sample holder and then is attached to a sample holder and separated from the probe.

Figure 2:
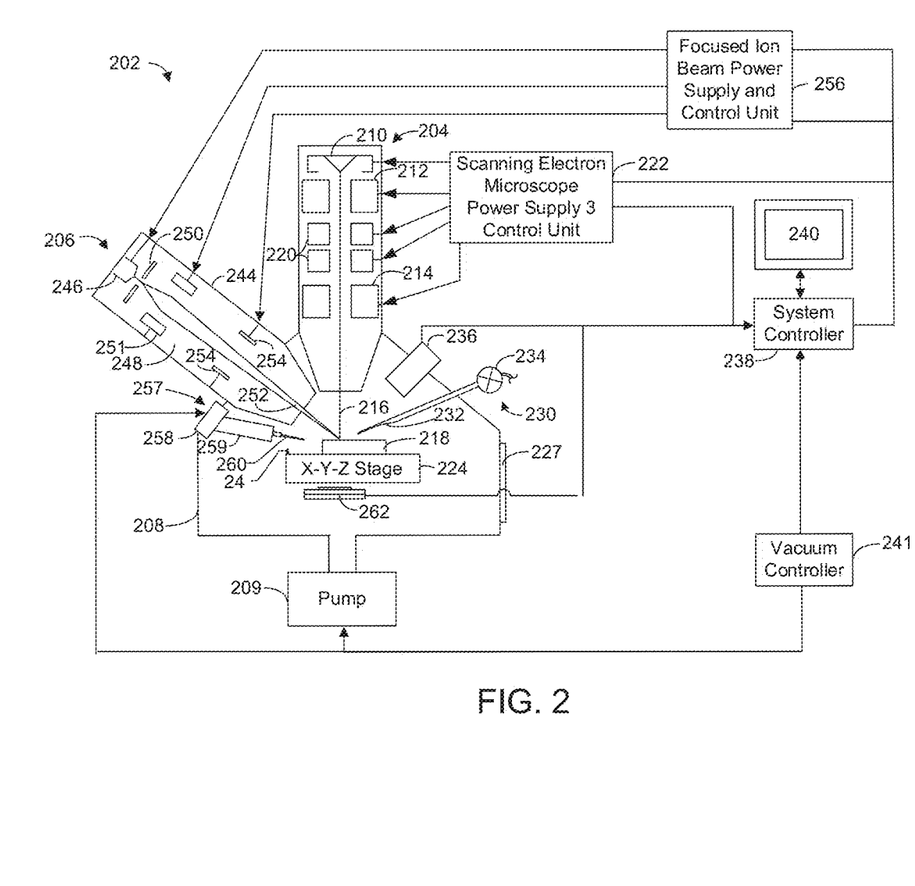
FIG. 2 shows schematically a dual beam system that can be used in an embodiment of the invention.

First, in step 102, a substrate such as a semiconductor wafer is loaded into a Dual Beam system having both a FIB column and a SEM column. Referring also to FIG. 2, the typical dual-beam system 202 configuration includes an electron column 204 having a vertical axis with an ion column 206 having an axis tilted with respect to the vertical (usually at a tilt of approximately 52 degrees). Wafers are preferably transferred by way of a multi-wafer carrier and auto-loading robot (not shown), as in well known in the art, although wafers can also be transferred manually. FIG. 2 is described in more detail below.

In step 104, the location of a sample (containing a feature of interest) to be extracted from a work piece substrate is determined. For example, the substrate may be a semiconductor wafer or portion thereof and the portion to be extracted may include a portion of an integrated circuit that is to be observed using the TEM. The location of the sample can be determined using a variety of methods known in the prior art. For example, the sample location can be located using coordinates based on CAD data for the semiconductor wafer. Lamella sites on the wafer surface can also be located automatically using image recognition software. Suitable image recognition software is available, for example, from Cognex Corporation of Natick, Mass. Image recognition software can be "trained" to locate the desired lamella locations by using sample images of similar features or by using geometric information from CAD data.

Figure 3:
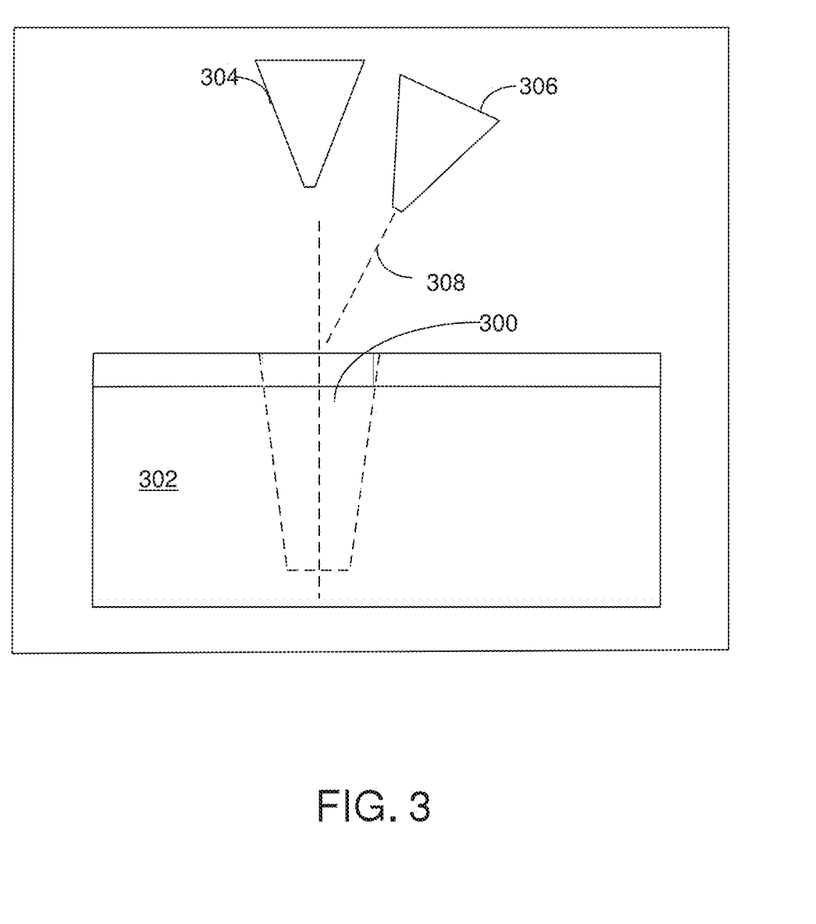
FIG. 3 is a simplified schematic representation showing the location of a TEM sample to be extracted within a larger substrate.

FIG. 3 is a schematic representation showing the location of the sample 300 to be extracted within a larger substrate 302 using a focused ion beam 308 from an ion beam column 306. The process can be observed using an electron beam from electron column 304. In some embodiments, a prepared sample can be observed using scanning transmission electron microscopy using electron column 304. FIGS. 4A-4D and FIG. 5A-5D are photomicrographs illustrating the process. In step 106, the sample 300 is partially separated from the substrate 302 by milling with a focused ion beam 308. Ion beam milling is used to refer to both sputtering without a gas assist and gas assisted ion beam etching.

Figure 4A:
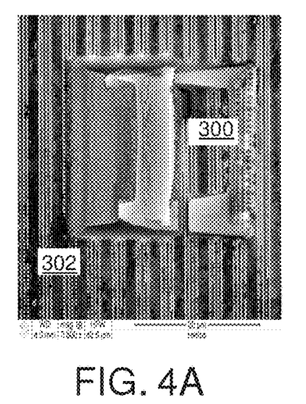
FIGS. 4A-4D are photomicrograph images showing the sequence of a typical in-situ lift out of a chunk-type TEM.
Figure 4B:
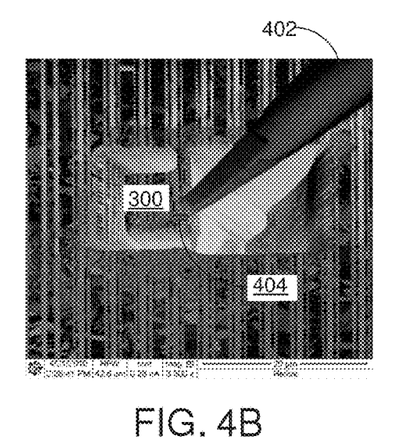

FIG. 4A shows the sample 300 partially milled in substrate 302. This step can be accomplished using an ion beam from a dual beam FIB/SEM system such as the Helios1200 Expida™ 1255 DualBeam™ System, available from FEI Company of Hillsboro, Oreg., the assignee of the present invention. Next, in step 108, the tip of a microprobe 402 is attached to the sample 300 by ion beam induced deposition as shown in FIG. 4B, which shows the deposited material 404 that attached the sample 300 to the probe tip 402. In ion beam induced deposition, a precursor gas, such as tungsten hexacarbonyl, is provided at the work piece surface. The precursor gas is decomposed in the presence of the ion beam to form a non-volatile portion that deposits on the surface and a volatile portion that is removed from the vacuum chamber by the vacuum pump. Many precursor gases are known and described, for example, in L. A. Giannuzzi and F. A. Stevens; *Introduction to Focused Ion Beams: Instrumentation, Theory, Techniques and Practice; Springer Press* (2004). When ion beam induced deposition is used to join parts together, it is referred to as ion beam welding.

Figure 4C:
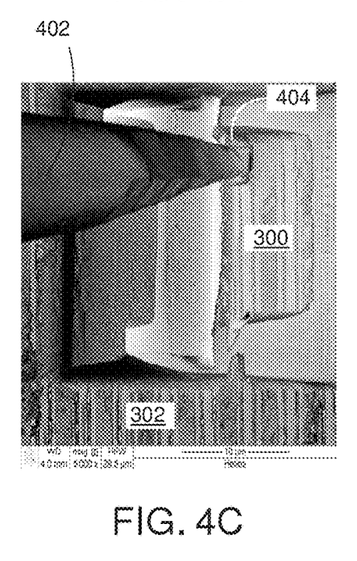
Figure 4D:
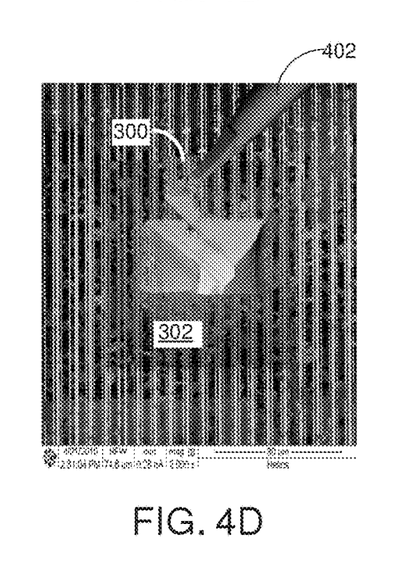

The sample is then completely freed by further FIB milling in step 110 and is supported by the probe as shown in FIG. 4C. This process typically results in a wedge-shaped sample 300, which is approximately 10 µm×5 µm×5 µm. In other embodiments, the sample could be in the form of a lamella. The invention is not limited to any specific sample shape. In step 112, the sample 300 is then lifted free of the substrate 302 using the attached microprobe 402 as shown in FIG. 4D.

Figure 5A:
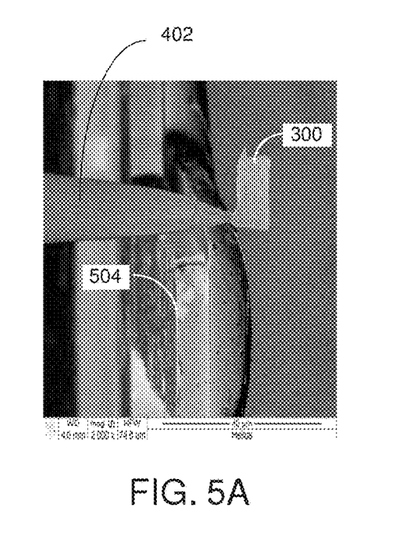
FIGS. 5A-5D are photomicrograph images showing the sequence of mounting a TEM sample on a TEM sample grid.
Figure 5B:
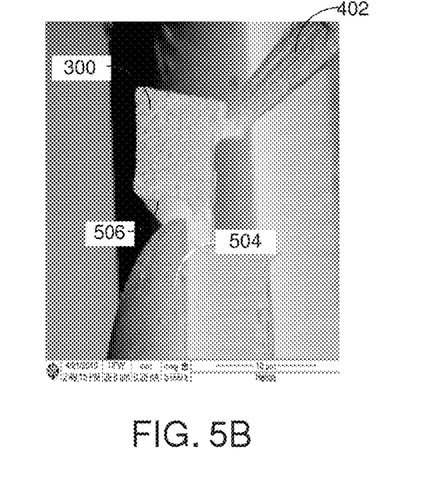
Figure 5C:
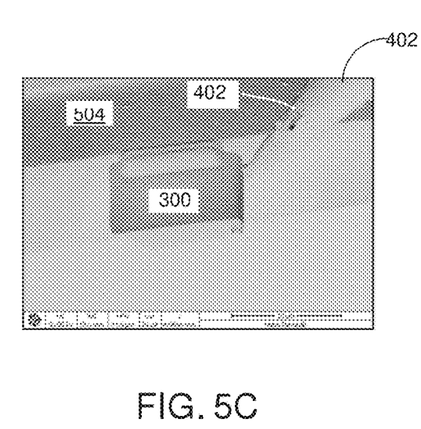
Figure 5D:
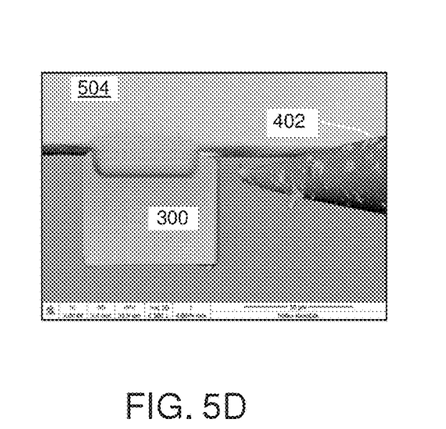

In step 114, the sample is then transported by the attached microprobe to a TEM sample holder 504 as shown in FIG. 5A FIGS. 5C and 5D show a different sample than the one in FIGS. 5A and 5B. The microprobe is preferably attached to a micromanipulator having multiple degrees of freedom for moving the probe tip within the vacuum chamber. Sample holder 504 can comprise, for example, a TEM finger grid typically having a three mm diameter and having "fingers" or a wire upon which to attach the sample. In some embodiments, the TEM sample holder is preferably mounted vertically onto a stage so that the vertical axis of TEM sample holder 504 is perpendicular to the plane of the sample stage surface. In the embodiment shown in FIG. 4A, the vertical axis of the sample is substantially parallel to the vertical axis of the TEM sample holder 504. Although other orientations are possible, this orientation is described herein for simplicity.

In optional step 116, in some embodiments the sample is then inverted by rotating the microprobe so that the substrate side of the sample is facing up (also referred to as the backside). In other words, the sample is rotated around an axis perpendicular to the sample's vertical axis in order to invert the top and bottom sides of the sample. FIG. 5B shows a top down view of the sample in close proximity to the TEM sample holder. In step 118, the sample 300 is attached to the sample holder 504 using ion-beam induced deposition, typically by depositing along most of the length of the sample edge near the sample holder.

In step 120, the probe is broken free from the sample by relative motion between the two. For example, the probe can be moved away from the sample attached to the TEM sample holder, or the stage holder the TEM sample holder can be moved as the grid is held stationary. The bond between the probe tip and the sample is typically smaller than the bond between the sample and the sample holder. The probe tip is welded to the sample at a point, whereas the sample is welded to the sample holder typically along a line. Applicant has found that when the sample holder and the probe are moved apart, the bond between the probe and the sample breaks without damaging the sample, and the sample remains attached to the sample holder.

The bond between the sample and the probe tip is not severed using ion beam milling. By mechanically severing the connection instead of ion beam milling, the probe tip does not become blunt and processing time required to cut through the tip with the ion beam is eliminated. The relative motion is preferably in a direction in which the bond between the probe and the sample is weak and the bond between the sample and the sample holder is stronger. FIG. 5D the probe freed from the sample by moving the probe away from the sample, leaving the sample attached to the sample holder 504. In step 122, the prepared sample is observed on a TEM or STEM.

The process described above can be partially or completely automated.

FIG. 2 depicts one embodiment of an exemplary dual beam SEM/FIB system 202 that is equipped to carry out a method according to the present invention. Suitable dual beam systems are commercially available, for example, from FEI Company, Hillsboro, Oreg., the assignee of the present application. While an example of suitable hardware is provided below, the invention is not limited to being implemented in any particular type of hardware.

Dual beam system 202 has a vertically mounted electron beam column 204 and a focused ion beam (FIB) column 206 mounted at an angle of approximately 52 degrees from the vertical on an evacuable specimen chamber 208. The specimen chamber may be evacuated by pump system 209, which typically includes one or more, or a combination of, a turbo-molecular pump, oil diffusion pumps, ion getter pumps, scroll pumps, or other known pumping means.

The electron beam column 204 includes an electron source 210, such as a Schottky emitter or a cold field emitter, for producing electrons, and electron-optical lenses 212 and 214 forming a finely focused beam of electrons 216. Electron source 210 is typically maintained at an electrical potential of between 500 V and 30 kV above the electrical potential of a work piece 218, which is typically maintained at ground potential.

Thus, electrons impact the work piece 218 at landing energies of approximately 500 eV to 30 keV. A negative electrical potential can be applied to the work piece to reduce the landing energy of the electrons, which reduces the interaction volume of the electrons with the work piece surface, thereby reducing the size of the nucleation site. Work piece 218 may comprise, for example, a semiconductor device, microelectromechanical system (MEMS), or a lithography mask. The impact point of the beam of electrons 216 can be positioned on and scanned over the surface of a work piece 218 by means of deflection coils 220. Operation of lenses 212 and 214 and deflection coils 220 is controlled by scanning electron microscope power supply and control unit 222. Lenses and deflection unit may use electric fields, magnetic fields, or a combination thereof.

Work piece 218 is on movable stage 224 within specimen chamber 208. Stage 224 can preferably move in a horizontal plane (X and Y axes) and vertically (Z axis) and can tilt approximately sixty (60) degrees and rotate about the Z axis. A door 227 can be opened for inserting work piece 218 onto X-Y-Z stage 224 and also for servicing an internal gas supply reservoir (not shown), if one is used. The door is interlocked so that it cannot be opened if specimen chamber 208 is evacuated.

Mounted on the vacuum chamber are multiple gas injection systems (GIS) 230 (two shown). Each GIS comprises a reservoir (not shown) for holding the precursor or activation materials and a needle 232 for directing the gas to the surface of the work piece. Each GIS further comprises means 234 for regulating the supply of precursor material to the work piece. In this example the regulating means are depicted as an adjustable valve, but the regulating means could also comprise, for example, a regulated heater for heating the precursor material to control its vapor pressure.

When the electrons in the electron beam 216 strike work piece 218, secondary electrons, backscattered electrons, and Auger electrons are emitted and can be detected to form an image or to determine information about the work piece. Secondary electrons, for example, are detected by secondary electron detector 236, such as an Everhard-Thornley detector, or a semiconductor detector device capable of detecting low energy electrons. STEM detector 262, located beneath the TEM sample holder 224 and the stage 225, can collect electrons that are transmitted through a sample mounted on the TEM sample holder. Signals from the detectors 236, 262 are provided to a system controller 238. Said controller 238 also controls the deflector signals, lenses, electron source, GIS, stage and pump, and other items of the instrument. Monitor 240 is used to display user controls and an image of the work piece using the signal The chamber 208 is evacuated by pump system 209 under the control of vacuum controller 241. The vacuum system provides within chamber 208 a vacuum of approximately 3×10−6 mbar. When a suitable precursor or activator gas is introduced onto the sample surface, the chamber background pressure may rise, typically to about 5×10−5 mbar.

Focused ion beam column 206 comprises an upper neck portion 244 within which are located an ion source 246 and a focusing column 248 including extractor electrode 250 and an electrostatic optical system including an objective lens 251. Ion source 246 may comprise a liquid metal gallium ion source, a plasma ion source, a liquid metal alloy source, or any other type of ion source. The axis of focusing column 248 is tilted 52 degrees from the axis of the electron column. An ion beam 252 passes from ion source 246 through focusing column 248 and between electrostatic deflectors 254 toward work piece 218.

FIB power supply and control unit 256 provides an electrical potential at ion source 246. Ion source 246 is typically maintained at an electrical potential of between 1 kV and 60 kV, more preferably between 20 kV and 40 kV, and most preferably about 30 kV, above the electrical potential of the work piece, which is typically maintained at ground potential. Thus, ions impact the work piece at landing energies of approximately 1 keV to 60 keV, more preferably between 20 keV and 40 keV, and most preferably about 30 keV. FIB power supply and control unit 256 is coupled to deflection plates 254 which can cause the ion beam to trace out a corresponding pattern on the upper surface of work piece In some systems, the deflection plates are placed before the final lens, as is well known in the art. Beam blanking electrodes (not shown) within ion beam focusing column 248 cause ion beam 252 to impact onto blanking aperture (not shown) instead of work piece 218 when a FIB power supply and control unit 256 applies a blanking voltage to the blanking electrode.

The ion source 246 typically provides a beam of singly charged positive gallium ions that can be focused into a sub one-tenth micrometer wide beam at work piece 218 for modifying the work piece 218 by ion milling, enhanced etch, material deposition, or for imaging the work piece 218.

A micromanipulator 257, such as the AutoProbe 200™ from Omniprobe, Inc., Dallas, Tex., or the Model MM3A from Kleindiek Nanotechnik, Reutlingen, Germany, can precisely move objects within the vacuum chamber. Micromanipulator 257 may comprise precision electric motors 258 positioned outside the vacuum chamber to provide X, Y, Z, and theta control of a portion 259 positioned within the vacuum chamber. The micromanipulator 257 can be fitted with different end effectors for manipulating small objects. In the embodiments described herein, the end effector is a thin probe 260. As is known in the prior art, a micromanipulator (or microprobe) can be used to transfer a TEM sample (which has been freed from a substrate, typically by an ion beam) to a TEM sample holder 261 for analysis.

System controller 238 controls the operations of the various parts of dual beam system 202. Through system controller 238, a user can cause ion beam 252 or electron beam 216 to be scanned in a desired manner through commands entered into a conventional user interface (not shown). Alternatively, system controller 238 may control dual beam system 202 in accordance with programmed instructions. FIG. 2 is a schematic representation, which does not include all the elements of a typical dual beam system and which does not reflect the actual appearance and size of, or the relationship between, all the elements.

In accordance with one aspect of some embodiments of the invention a method is provided of preparing a sample for TEM analysis, the method comprising: loading a substrate into an ion beam system; separating a sample from the substrate by ion beam milling; attaching the sample to a probe; transporting the sample to a sample holder; attaching the sample to the sample holder using charged particle beam induced deposition; separating the probe from the sample holder by moving the probe or sample relative to each other without cutting the sample from the probe before moving.

In some embodiments, attaching the sample to the sample holder includes attaching the sample to the sample holder using ion-beam induced deposition.

In some embodiments, separating the probe from the sample holder by moving the probe or sample relative to each other includes separating the probe from the sample holder by moving the probe.

In some embodiments, separating the probe from the sample holder by moving the probe or sample relative to each other includes separating the probe from the sample holder by moving the sample holder.

In some embodiments, attaching the sample to the sample holder includes attaching the sample to a toothed, 3 mm TEM sample holder.

In some embodiments, separating a sample from the substrate by ion beam milling includes separating a lamella.

In some embodiments, separating a sample from the substrate by ion beam milling includes separating a chunk.

In some embodiments, separating a sample from the substrate by ion beam milling includes separating planar view sample.

In some embodiments, separating a sample from the substrate by ion beam milling includes separating a cross sectional view sample.

In some embodiments, separating a sample from the substrate by ion beam milling includes separating a sample having a viewing area that is less than 50 nm thick.

In some embodiments, separating a sample from the substrate by ion beam milling includes separating a sample comprising silicon In accordance with an aspect of the some embodiments of the invention, a system is provided for preparing a TEM sample, the comprising a source of charged particles; a lens for focusing the changed particles onto a work piece; a work piece holder for holding a work piece, the work piece holder capable for moving in at least two dimensions; a sample holder for holding a sample severed from the work piece; a movable prove for moving the sample severed from the work to the sample holder; a source of a precursor gas for charged particle beam deposition to attach the sample severed from the work piece to the sample holder; a computer for controlling the system, the computer programmed to: separate a sample from the substrate by ion beam milling; attach the sample to a probe; transport the sample to a sample holder; attach the sample to the sample holder using charged particle beam induced deposition; separate the probe from the sample holder by moving the probe or sample relative to each other without cutting the sample from the probe before moving.

In some embodiments, the computer is programmed to separate the probe from the sample holder by moving the probe.

Another aspect of the some embodiments of the invention includes a computer readable medium storing computer instructions to: separate a sample from the substrate by ion beam milling; attach the sample to a probe; transport the sample to a sample holder; attach the sample to the sample holder using charged particle beam induced deposition; and separate the probe from the sample holder by moving the probe or sample relative to each other without cutting the sample from the probe before moving.

It should be recognized that embodiments of the present invention can be implemented via computer hardware, a combination of both hardware and software, or by computer instructions stored in a non-transitory computer-readable memory. The methods can be implemented in computer programs using standard programming techniques—including a non-transitory computer-readable storage medium configured with a computer program, where the storage medium so configured causes a computer to operate in a specific and predefined manner—according to the methods and figures described in this Specification.

Aspects of the present invention may be implemented in machine readable code stored on a storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of computer-readable storage media when such media contain instructions or programs for implementing the steps described above in conjunction with a microprocessor or other data processor. The invention also includes the computer itself when programmed according to the methods and techniques described herein.

Preferred embodiments of the present invention also make use of a particle beam apparatus, such as a FIB or SEM, in order to image a sample using a beam of particles. Such particles used to image a sample inherently interact with the sample resulting in some degree of physical transformation. Further, throughout the present specification, discussions utilizing terms such as "calculating," "determining," "measuring," "generating," "detecting," "forming," or the like, also refer to the action and processes of a computer system, or similar electronic device, that manipulates and transforms data represented as physical quantities within the computer system into other data similarly represented as physical quantities within the computer system or other information storage, transmission or display devices.

Although much of the previous description is directed at semiconductor wafers, the invention could be applied to any suitable substrate or surface. Further, whenever the terms "automatic," "automated," or similar terms are used herein, those terms will be understood to include manual initiation of the automatic or automated process or step. In the following discussion and in the claims, the terms "including" and "comprising" are used in an open-ended fashion, and thus should be interpreted to mean "including, but not limited to . . . ." The term "integrated circuit" refers to a set of electronic components and their interconnections (internal electrical circuit elements, collectively) that are patterned on the surface of a microchip. The term "semiconductor device" refers generically to an integrated circuit (IC), which may be integral to a semiconductor wafer, singulated from a wafer, or packaged for use on a circuit board. The term "FIB" or "focused ion beam" is used herein to refer to any collimated ion beam, including a beam focused by ion optics and shaped ion beams.

To the extent that any term is not specially defined in this specification, the intent is that the term is to be given its plain and ordinary meaning. The accompanying drawings are intended to aid in understanding the present invention and, unless otherwise indicated, are not drawn to scale.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

I claim as follows:

1. A method of preparing a sample for TEM analysis, the method comprising: loading a substrate into an ion beam system;
   separating a sample from the substrate by ion beam milling;
   attaching the sample to a probe using charged particle beam-induced deposition to form a bond between the sample and the probe;
   transporting the sample to a sample holder;
   attaching the sample to the sample holder using charged particle beam induced deposition to form a bond between the sample and the sample holder; and
   separating the probe from the sample by moving, without cutting the sample from the probe before moving, the probe or sample holder relative to each other in a direction in which the bond between the sample and the sample holder is stronger than the bond between the sample and the probe.

2. The method of claim 1 in which separating the probe from the sample by moving the probe or sample holder relative to each other includes separating the probe from the sample holder by moving the probe.

3. The method of claim 1 in which separating the probe from the sample by moving the probe or sample holder relative to each other includes separating the probe from the sample by moving the sample holder.

4. The method of claim 1 in which attaching the sample to the sample holder includes attaching the sample to a toothed, 3 mm TEM sample holder.

5. The method of claim 1 in which separating a sample from the substrate by ion beam milling includes separating a lamella.

6. The method of claim 1 in which separating a sample from the substrate by ion beam milling includes separating a chunk.

7. The method of claim 1 in which separating a sample from the substrate by ion beam milling includes separating a planar view sample.

8. The method of claim 1 in which separating a sample from the substrate by ion beam milling includes separating a cross sectional view sample.

9. The method of claim 1 in which separating a sample from the substrate by ion beam milling includes separating a sample having a viewing area that is less than 50 nm thick.

10. The method of claim 1 in which separating a sample from the substrate by ion beam milling includes separating a sample comprising silicon.

11. A system for preparing a TEM sample, comprising:
    a source of charged particles;
    a lens for focusing the changed particles onto a work piece;
    a work piece holder for holding a work piece, the work piece holder capable for moving in at least two dimensions;
    a sample holder for holding a sample severed from the work piece;
    a movable probe for moving the sample severed from the work to the sample holder;
    a source of a precursor gas for charged particle beam deposition to attach the sample severed from the work piece to the sample holder;
    a computer for controlling the system, the computer programmed to:
      separate a sample from a substrate by ion beam milling;
      attach the sample to a probe using charged particle beam-induced deposition to form a bond between the sample and the probe;
      transport the sample to a sample holder;
      attach the sample to the sample holder using charged particle beam induced deposition to form a bond between the sample and the sample holder, the bond between the sample and the sample holder being stronger than the bond between the sample and the probe;
      separate the probe from the sample by moving the probe or sample holder relative to each other without cutting the sample from the probe before moving.

12. The system of claim 11 in which the computer is programmed to separate the probe from the sample by moving the probe.

13. The method of claim 1 in which the bond between the probe and the sample is smaller than the bond between the sample and the sample holder.

14. The method of claim 1 wherein the sample is attached to the probe at a point and the sample is attached to sample holder along a line.

* * * * *